United States Patent [19]

Takase et al.

[11] Patent Number: 4,545,932
[45] Date of Patent: Oct. 8, 1985

[54] GLUCOSAMINYL MURAMYL PEPTIDE DERIVATIVES

[75] Inventors: Yoshiyuki Takase, Amagasaki; Ryuji Furuta, Otsu; Shigeo Kawata, Kobe; Shunsuke Naruto, Ikoma; Shinichi Nakamura, Takatsuki; Akira Minami, Hirakata, all of Japan

[73] Assignee: Dainippon Pharmaceutical Co., Ltd., Osaka, Japan

[21] Appl. No.: 494,336

[22] Filed: May 13, 1983

[30] Foreign Application Priority Data

May 14, 1982 [JP] Japan .................................. 57-82178

[51] Int. Cl.$^4$ .......................................... C07C 103/52
[52] U.S. Cl. ............................................ 260/112.5 R
[58] Field of Search .............................. 260/112.5 R

[56] References Cited

PUBLICATIONS

Chemical Abstracts, 100, 640 (1984), Abst. No. 68710v.
Chemical Abstracts, 99, 529 (1983), Abst. No. 211141d.
Chemical Abstracts, 86, 169 (1977), Abst. No. 151982y.
Chemical Abstracts, 96, 750 (1982), Abst. No. 181627k.
Dezelee et al., *Biochemistry,* 11, No. 4, 823-831, (1970).
Ellouz et al., *Biochem. & Biophysical Res. Commu.,* 59, No. 4, 1317-1325, (1974).
Yamamura et al., *Proc. Japan Acad.,* 52, 58-61, (1976).

Primary Examiner—Delbert R. Phillips
Assistant Examiner—F. T. Moezie
Attorney, Agent, or Firm—Wegner & Bretschneider

[57] ABSTRACT

Novel glucosaminyl muramyl peptide derivatives of the formula:

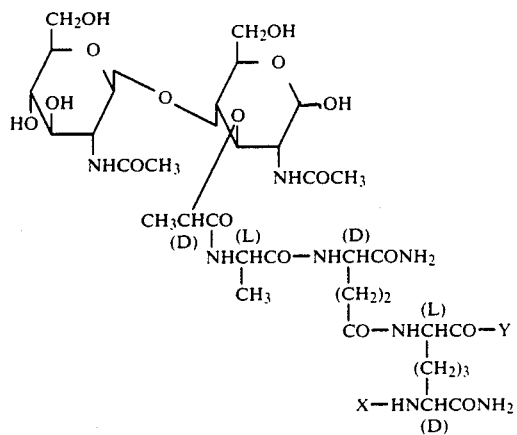

wherein X is hydrogen atom or a group of the formula: $R_1CO-$, Y is hydroxy group or a group of the formula: $-OR_2$,

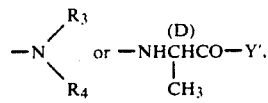

$R_1$ is an alkyl or alkenyl group, $R_2$ is a lower alkyl group or a phenylalkyl group, $R_3$ and $R_4$ are the same or different and are each hydrogen atom or an alkyl group, Y' is hydroxy group or a group of the formula: $-OR_2$ or

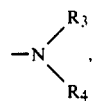

(D) and (L) mean the configuration, provided that when X is hydrogen atom, Y is a group of the formula:

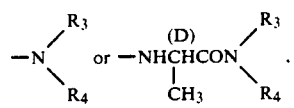

and their pharmaceutically acceptable salts. They have excellent biological activities such as potentiating activity of nonspecific resistance to microbial infections and immunostimulant activity and hence are useful in the prophylaxis and treatment of various microbial infections.

14 Claims, No Drawings

GLUCOSAMINYL MURAMYL PEPTIDE DERIVATIVES

The present invention relates to novel glucosaminyl muramyl peptide derivatives having potentiating activity of nonspecific resistance to microbial infections, immunostimulant activity, and the like.

German patent Publication (unexamined) No. 28 47 608 discloses a compound of the formula (I).

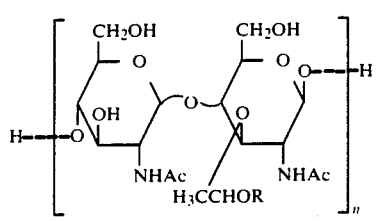

wherein n is 1 or 2, and R is an amino acid residue or a peptide residue, wherein it is stated that said compound shows antitumor activity. However, this German patent discloses merely five specific compounds, i.e. a compound of the formula (I) wherein n is 1 and R is L-alanine residue, L-alanyl-D-isoglutamine, L-alanyl-D-glutamic acid or L-N$^\epsilon$-(L-alanyl-D-glutamyl-D-isoasparaginyl)lysyl-D-alanine amide, and a compound of the formula (I) wherein n is 2 and R is L-alanyl-D-isoglutamine.

U.S. Pat. No. 4,186,194 discloses a compound of the formula (II) or (III):

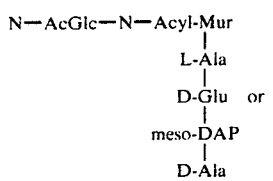 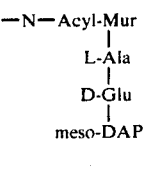

wherein N-AcGlc is N-acetylglucosaminyl group, N-Acyl-Mur is N-acylmuramyl group, L-Ala is L-alanyl group, D-Glu is D-glutamyl group, meso-DAP is meso-2,6-diaminopimelyl group or meso-2,6-diaminopimelic acid residue, and D-Ala is D-alanine residue, provided that the carboxyl group at the alpha position in D-glutamic acid residue and/or one carboxyl group in meso-2,6-diaminopimelic acid residue may be either in a free state or amidated, in addition to other peptidoglycans having a low molecular weight, wherein it is stated that said compound of the formula (II) or (III) has an immunostimulant activity. The process disclosed in this U.S. patent comprises applying a lytic enzyme to hydrolyze cell walls of *Mycobacteria, Nocardiae* or *Escherichia coli*. However, they have merely obtained a compound of the formula (II), wherein Acyl is glycolyl group and the carboxyl group of glutamyl and meso-2,6-diaminopimelyl groups is amidated, by hydrolyzing delipidated cell walls by the catalysis of lysozyme and muramyl-L-alanine amidase from Myxobacter AL$_1$ to produce three fractions of peptidoglycans and subjecting one fraction with the lowest molecular weight to preparative electrophoresis.

The present inventors had found that two compounds of the formula (IV):

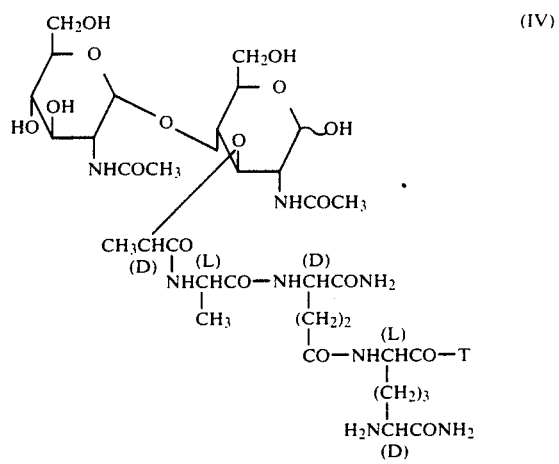

wherein T is hydroxy group or D-alanine residue, can be produced by applying an endo-N-acetylmuramidase and a D-alanyl-meso-2,6-diaminopimelic acid endopeptidase from *Streptomyces globisporus* to hydrolyze alkali-treated cell walls of *Lactobacillus plantarum* (cf. German Patent Application P33 01 997.5). These compounds are β-N-acetylglucosaminyl-(1→4)-N-acetylmuramyl-L-alanyl-D-isoglutaminyl-(L)-meso-2,6-diaminopimelic acid-(D)-amide (hereinafter referred to as "GMP$_3$-A") and β-N-acetylglucosaminyl-(1→4)-N-acetylmuramyl-L-alanyl-D-isoglutaminyl-(L)-meso-2,6-diaminopimelic acid-(D)-amide-(L)-D-alanine (hereinafter referred to as "GMP$_4$-A") and have biological activities such as immunostimulant activity and potentiating activity of nonspecific resistance to microbial infections.

As a result of further extensive study of the present inventors, it has been found that acylation of the amino group of diaminopimelic acid residue in GMP$_3$-A and GMP$_4$-A and/or amidation of the carboxyl group of diaminopimelic acid residue in GMP$_3$-A or of alanine residue in GMP$_4$-A gives novel glucosaminyl muramyl peptide derivatives exhibiting more potent antiinfectious activity and/or less side effects (e.g. less pyrogenicity) than the parent compound, GMP$_3$-A or GMP$_4$-A.

An object of the present invention is to provide novel glucosaminyl muramyl peptide derivatives having excellent biological activities such as potentiating activity of nonspecific resistance to microbial infections, immunostimulant activity, or the like. Another object of the invention is to provide an improvement of properties of GMP$_3$-A and GMP$_4$-A by chemical modification thereof. These and other objects and advantages of the present invention will be apparent to persons skilled in the art from the following description.

The compounds of the present invention are glucosaminyl muramyl peptide derivatives of the formula (V):

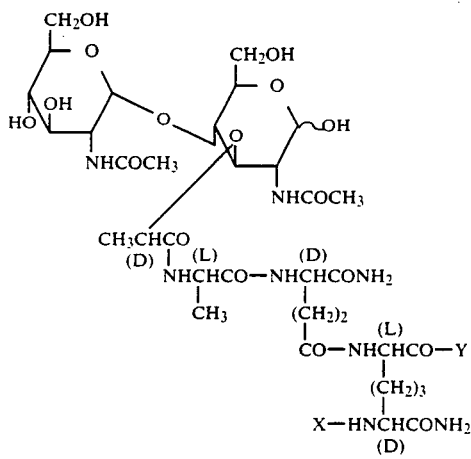
 (V)

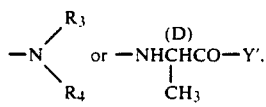

wherein X is hydrogen atom or a group of the formula: $R_1CO-$, Y is hydroxy group or a group of the formula: $-OR_2$,

$R_1$ is an alkyl or alkenyl group, $R_2$ is a lower alkyl group or a phenylalkyl group, $R_3$ and $R_4$ are the same or different and are each hydrogen atom or an alkyl group, Y' is hydroxy group or a group of the formula: $-OR_2$ or

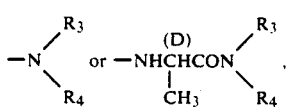

(D) and (L) mean the configuration, provided that when X is hydrogen atom, Y is a group of the formula:

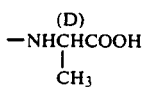

or pharmaceutically acceptable salts thereof.

The pharmaceutically acceptable salt of the present invention includes a salt of a compound of the formula (V) wherein Y is hydroxy group or a group of the formula:

with an inorganic or organic base, and a salt of a compound of the formula (V) wherein X is hydrogen atom with an inorganic or organic acid. Examples of the salts with an inorganic base are sodium, potassium, calcium, magnesium, aluminum, and ammonium salts. Examples of the salts with an organic base are the salts with isopropylamine, diethylamine, ethanolamine, and piperidine. Examples of the salts with inorganic acid are hydrochloride, hydrobromide, hydroiodide, sulfate, and phosphate, and those with an organic acid are methanesulfonate.

In the present specification, the term "alkyl group" denotes a straight or branched alkyl group having 1 to 30 carbon atoms, preferably a straight alkyl group having 1 to 21 carbon atoms. The term "alkenyl group" denotes a straight or branched alkenyl group having 1 to 4 double bonds and having 2 to 30 carbon atoms, preferably a straight alkenyl group having 1 to 2 double bonds and having 2 to 21 carbon atoms. The term "lower alkyl group" denotes a straight or branched alkyl group having 1 to 6 carbon atoms, preferably 1 to 4 carbon atoms. The term "phenylalkyl group" denotes a phenyl-substituted straight or branched alkyl group having 1 to 3 carbon atoms in the alkyl moiety, for example benzyl and phenethyl.

The group of the formula: $R_1CO-$ includes, for example, acetyl, propionyl, butyryl, isobutyryl, valeryl, isovaleryl, hexanoyl, heptanoyl, octanoyl, 2-ethylhexanoyl, decanoyl, lauroyl, myristoyl, palmitoyl, stearoyl, eicosanoyl, docosanoyl, tetracosanoyl, hexacosanoyl, octacosanoyl, triacontanoyl, acryloyl, methacryloyl, crotonoyl, isocrotonoyl, 4-dodecenoyl, 9-tetradecenoyl, 9-hexadecenoyl, oleoyl, elaidoyl, 9,12-octadecadienoyl, 13,16-docosadienoyl, 17,20-hexacosadienoyl, or the like.

The group of the formula:

includes, for example, amino, methylamino, ethylamino, propylamino, isopropylamino, butylamino, isobutylamino, pentylamino, hexylamino, heptylamino, octylamino, nonylamino, decylamino, undecylamino, dodecylamino, tridecylamino, tetradecylamino, pentadecylamino, hexadecylamino, heptadecylamino, octadecylamino, nonadecylamino, eicosylamino, dimethylamino, diethylamino, dipropylamino, dibutylamino, dipentylamino, dihexylamino, diheptylamino, N-methylethylamino, N-methylpropylamino, N-methylbutylamino, N-methylpentylamino, N-methyldodecylamino, N-ethylpropylamino, N-ethylpentylamino, or the like, among which amino and monoalkyl-substituted amino groups are preferable.

Preferred compounds of the present invention are compounds of the formula (V) wherein X is a group of the formula: $R_1CO-$ wherein $R_1$ is a straight alkyl group having 1 to 21 carbon atoms or a straight alkenyl group having 1 to 2 double bonds and having 2 to 21 carbon atoms; and Y is hydroxy group, an alkoxy group having 1 to 4 carbon atoms, benzyloxy group, amino group, an amino group mono-substituted by a straight alkyl group having 1 to 21 carbon atoms, or a group of the formula:

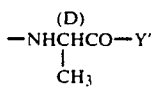

wherein Y' is hydroxy group, an alkoxy group having 1 to 4 carbon atoms, benzyloxy group, amino group, or an amino group mono-substituted by a straight alkyl group having 1 to 21 carbon atoms; and compounds of the formula (V) wherein X is hydrogen atom; and Y is amino group, an amino group mono-substituted by a straight alkyl group having 1 to 21 carbon atoms, or a group of the formula:

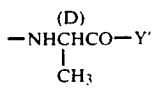

wherein Y' is amino group or an amino group mono-substituted by a straight alkyl group having 1 to 21 carbon atoms; and a pharmaceutically acceptable salt thereof.

More preferred compounds are compounds of the formula (V) wherein X is a group of the formula $R_1CO$— wherein $R_1$ is a straight alkyl group having 11 to 17 carbon atoms or a straight alkenyl group having 1 to 2 double bonds and having 11 to 17 carbon atoms, and Y is hydroxy group, an alkoxy group having 1 to 4 carbon atoms or benzyloxy group; compound of the formula (V) wherein X is a group of the formula: $R_1CO$— wherein $R_1$ is a straight alkyl group having 11 to 17 carbon atoms, and Y is a group of the formula:

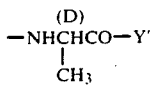

wherein Y' is hydroxy group, an alkoxy group having 1 to 4 carbon atoms or benzyloxy group; compounds of the formula (V) wherein X is hydrogen atom or a group of the formula: $R_1CO$— wherein $R_1$ is a straight alkyl group having 1 to 4 carbon atoms, and Y is amino group or an amino group mono-substituted by a straight alkyl group having 1 to 21 carbon atoms; compounds of the formula (V) wherein X is a group of the formula: $R_1CO$— wherein $R_1$ is a straight alkyl group having 11 to 17 carbon atoms or a straight alkenyl group having 1 to 2 double bonds and having 11 to 17 carbon atoms, Y is amino group or an amino group mono-substituted by a straight alkyl group having 1 to 4 carbon atoms; and a pharmaceutically acceptable salt thereof.

Particularly preferred compounds are compounds of the formula (V) wherein X is stearoyl or palmitoyl group, and Y is a group of the formula:

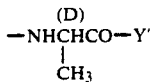

wherein Y' is hydroxy group, a straight alkoxy group having 1 to 4 carbon atoms or benzyloxy group; compounds of the formula (V) wherein X is hydrogen atom or acetyl group, and Y is amino group or an amino group mono-substituted by a straight alkyl group having 1 to 18 carbon atoms; compounds of the formula (V) wherein X is oleoyl group and Y is amino group; and a pharmaceutically acceptable salt thereof.

Specifically preferred compounds are compounds of the formula (V) wherein X is stearoyl or palmitoyl group and Y is a group of the formula:

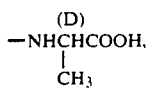

that is, the following two compounds and a pharmaceutically acceptable salt thereof, among which the first one and a pharmaceutically acceptable salt (particularly sodium salt) thereof are more preferable.

β-N-Acetylglucosaminyl-(1→4)-N-acetylmuramyl-L-alanyl-D-isoglutaminyl-(L)-stearoyl-(D)-meso-2,6-diaminopimelic acid-(D)-amide-(L)-D-alanine.

β-N-Acetylglucosaminyl-(1→4)-N-acetylmuramyl-L-alanyl-D-isoglutaminyl-(L)-palmitoyl-(D)-meso-2,6-diaminopimelic acid-(D)-amide-(L)-D-alanine.

The present compounds of the formula (V) can be prepared from the compounds of the formula (IV) (i.e. GMP$_3$-A or GMP$_4$-A) by a conventional method in the field of peptide synthesis (cf. E. Gross and J. Meienhofer (ed.), "The Peptides", Vol. 1, Academic Press, New York, 1979, and Barton and Ollis (ed.), "Comprehensive Organic Chemistry", Vol. 5, pp. 321–366, Pergamon Press, Oxford, 1979). The method is explained below, wherein the following abbreviations are occasionally used.

| | |
|---|---|
| Glc: | glucosaminyl |
| Mur: | muramyl |
| Ala: | alanyl |
| isoGln: | isoglutaminyl |
| A$_2$pm: | 2,6-diaminopimelyl |
| 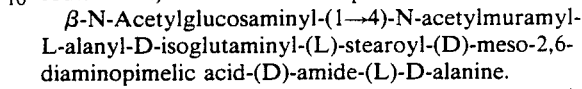 | meso-2,6-diaminopimelic acid residue |
| 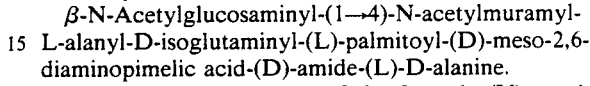 | |
| MDP: | N—acetylmuramyl-L-alanyl-D-isoglutaminyl |
| Ac: | acetyl |
| Dec: | decanoyl |
| Pal: | palmitoyl |
| Ste: | stearoyl |
| Ole: | oleoyl |
| Octd: | octadecyl |
| Me: | methyl |
| Bzl: | benzyl |
| Boc: | t-butoxycarbonyl |

By using these abbreviations, the formula (IV) can be represented as follows:

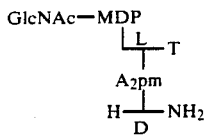

The compounds of the formula (V) wherein X is a group of the formula: $R_1CO$— and Y is a group other than those of the formula:

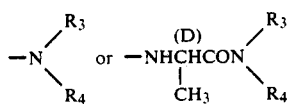

can be prepared, for example, by reacting a compound of the formula (VI):

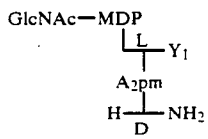
(VI)

wherein $Y_1$ is hydroxy group, or a group of the formula: $-OR_2$ or $$-\underset{\underset{CH_3}{|}}{N}H\underset{}{C}H\overset{(D)}{C}O-Y_1'.$$

$Y_1'$ is hydroxy group or a group of the formula: $-OR_2$, and $R_2$ is as defined above, with a compound of the formula: (VII):

$$R_1COOH \qquad (VII)$$

wherein $R_1$ is as defined above, or a reactive derivative thereof.

The reactive derivative of the compound (VII) includes, for example, activated esters, acid anhydrides, and acid halides (particularly acid chlorides). Suitable examples of the activated esters are p-nitrophenyl esters, 2,4,5-trichlorophenyl esters, pentachlorophenyl esters, cyanomethyl esters, N-hydroxysuccinimide esters, N-hydroxyphthalimide esters, N-hydroxy- 5-norbornene-2,3-dicarboximide esters, N-hydroxypiperidine esters, 8-hydroxyquinoline esters, 2-hydroxyphenyl esters, 2-hydroxy-4,5-dichlorophenyl esters, 2-hydroxypyridine esters, 2-pyridylthiol esters, or the like. The acid anhydrides include both of symmetrical anhydrides and mixed anhydrides, and suitable examples of the mixed anhydrides are mixed anhydrides formed with acids such as alkylcarbonic acids (e.g. ethylcarbonic acid or isobutylcarbonic acid), arylcarbonic acids (e.g. phenylcarbonic acids), and alkylcarboxylic acids (e.g. isovaleric acid or pivalic acid).

The reaction of the compound (VI) and the compound (VII) is usually carried out in the presence of a coupling reagent such as dicyclohexylcarbodiimide, 1-ethyl-3-(3-dimethylaminopropyl)carbodiimide, N,N'-carbonyldiimidazole, 1-ethoxycarbonyl-2-ethoxy-1,2-dihydroquinoline. When dicyclohexylcarbodiimide is used as the coupling reagent, there may be added N-hydroxysuccinimide, 1-hydroxybenzotriazole, 3-hydroxy-4-oxo-3,4-dihydro-1,2,3-benzotriazine, N-hydroxy-5-norbornene-2,3-dicarboximide, or the like to the reaction system.

The reaction of the compound (VI) and the compound (VII) or a reactive derivative thereof is usually carried out in a solvent. Suitable solvent may be selected depending on the kinds of starting materials, and includes, for example, tetrahydrofuran, dioxane, dimethylformamide, dimethyl sulfoxide, and water, which may be used alone or in combination of two or more thereof. The reaction may optionally be done in the presence of a base, such as alkali metal bicarbonates (e.g. sodium bicarbonate or potassium bicarbonate), alkali metal carbonates (e.g. sodium carbonate or potassium carbonate), organic bases (e.g. triethylamine, tri-n-butylamine, diisopropylethylamine, N-methylmorpholine, or dicyclohexylamine). The reaction temperature may vary with the kinds of starting materials, but is usually in the range of about −40° C. to about 50° C.

The compound (VI) wherein $Y_1$ is a group of the formula: $-OR_2$ or $$-\underset{\underset{CH_3}{|}}{N}H\underset{}{C}HCOOR_2 \qquad (D)$$

can be prepared, for example, by reacting a compound of the formula (IV) with an alcohol of the formula: $R_2OH$ in the presence of a mineral acid (as a catalyst).

The compounds of the formula (V) wherein Y is a group of the formula:

$$-N\diagup_{R_4}^{R_3} \quad or \quad -NHCHCON\diagup_{R_4}^{R_3}$$
$$\phantom{-NHCHCON}\underset{CH_3}{|}^{(D)}$$

can be prepared, for example, by reacting a compound of the formula (VIII):

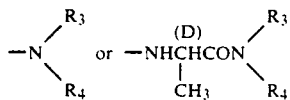
(VIII)

wherein X' is a group of the formula: $R_1CO-$ or an amino-protecting group, $Y_2$ is hydroxy group or a group of the formula;

$$-\underset{\underset{CH_3}{|}}{N}H\underset{}{C}HCOOH. \qquad (D)$$

and $R_1$ is as defined above, or a reactive derivative at carboxyl group thereof with an amine of the formula (IX):

$$HN\diagup_{R_4}^{R_3} \qquad (IX)$$

wherein $R_3$ and $R_4$ are as defined above, when X' is an amino-protecting group, followed by removing the protecting group.

The reactive derivative at carboxyl group of the compound (VIII) includes, for example, activated esters and acid anhydrides (particularly mixed anhydrides). Suitable examples of the reactive derivative are the same as those used in the reaction of the compound (VI) and the compound (VII) as mentioned hereinbefore. Suitable examples of the amino-protecting group are benzyloxycarbonyl, p-methoxybenzyloxycarbonyl, t-butoxycarbonyl, or isobornyloxycarbonyl group.

The reaction of the compound (VIII) or a reactive derivative at carboxyl group thereof and the compound (IX) is carried out under the same conditions as in the reaction of the compound (VI) and the compound (VII) or a reactive derivative thereof as mentioned hereinbefore.

When the reaction product contains an amino-protecting group, the protecting group can be removed by a conventional method, for example, by treating it with hydrogen bromide/trifluoroacetic acid, anhydrous hydrofluoric acid, trifluoroacetic acid, or the like. In this reaction, anisole may be added to the reaction system.

The compounds of the formula (V) wherein Y is a group of the formula: —OR$_2$ or

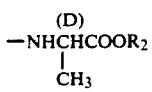

can also be prepared by esterifying a compound of the formula (Va):

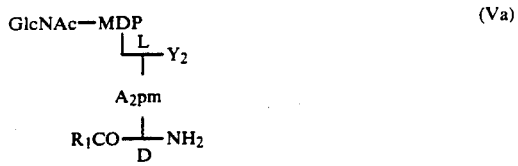

wherein R$_1$ and Y$_2$ are as defined above, by a conventional method, for example, by reacting an alkali metal salt (e.g. sodium or potassium salt) of the compound (Va) with a compound of the formula (X):

$$Z\text{-}R_2 \quad (X)$$

wherein R$_2$ is as defined above, and Z is a residue of a reactive ester of an alcohol.

The residue of a reactive ester of an alcohol for Z in the formula (X) includes, for example, halogen atoms (e.g. chlorine, bromine, or iodine) and organic sulfonyloxy group (e.g. benzenesulfonyloxy, p-toluenesulfonyloxy, or methanesulfonyloxy).

The esterification reaction is usually carried out in a solvent, such as methanol, ethanol, isopropyl alcohol, dimethylformamide, or the like. The reaction temperature is usually in the range of from room temperature to about 60° C.

The compounds (V) produced by the above methods can be isolated from the reaction mixture, purified and converted into a salt thereof by conventional methods. For example, the isolation and purification can be done by extraction, ion exchange chromatography, gel filtration, liquid chromatography, reprecipitation, or the like. When the compound of the formula (V) wherein Y is hydroxy group or a group of the formula:

is obtained in the form of a salt with a base, it can easily be converted into a free carboxylic acid by a conventional method, for example, by treating an aqueous solution of the salt with an ion exchanger or by treating it with a dilute mineral acid (e.g. dilute hydrochloric acid or dilute sulfuric acid), followed by desalting.

The starting materials used in the above methods, that is, the compound of the formula (IV) wherein T is hydroxy group or D-alanine residue (i.e. GMP$_3$-A or GMP$_4$-A), for example, can be prepared by applying an endo-N-acetylmuramidase and D-alanyl-meso-2,6-diaminopimelic acid endopeptidase from *Streptomyces globisporus* B-1829 (ATCC 21553) to hydrolyze alkali-treated cell walls of *Lacto bacillus plantarum* ATCC 8014, as disclosed in reference examples given hereinafter. The "endo-N-acetylmuramidase" means an enzyme which hydrolyzes the glycosidic linkages between N-acetylmuramic acid and N-acetylglucosamine, releasing fragments with N-acetylmuramic acid residues at the reducing end, and the "D-alanyl-meso-2,6-diaminopimelic acid endopeptidase" means an enzyme which can specifically split the D-alanyl-meso-2,6-diaminopimelic acid linkages between peptide subunits in bacterial cell wall peptidoglycans.

The compounds of the formula (V) and a pharmaceutically acceptable salt thereof have excellent biological activities such as potentiating activity of nonspecific resistance to microbial infections and immunostimulant activity, and are useful as an antiinfectious agent, or the like.

The properties such as antiinfectious activity, pyrogenicity and toxicity of representative compounds of the present invention were tested. The results are shown below.

(1) Prophylactic effect on the experimental infections

Std-ddY male mice weighing about 23 g (each group: 8 mice) were used. Test compounds dissolved in a physiological saline solution were each intravenously administered to mice once a day 1, 2 and 3 days before the infection. Twenty-four hours after the final administration of test compounds, the mice were infected with various microorganisms suspended in saline (in case of *Staphylococcus aureus* and *Candida albicans*) or in Trypto-Soy Broth (manufactured by Eiken Chemical Co., Ltd., Japan) (in case of *Pseudomonas aeruginosa* and *Escherichia coli*) under the conditions as shown in Table 1. The antiinfectious efficacy of test compounds was judged based on the survival ratio of mice on the date as shown in Table 1. When the experiment was repeated twice or more, the data were pooled. The results are shown in Table 2.

TABLE 1

| Microorganism | Inoculum size | Infection route | Efficacy judge |
|---|---|---|---|
| *Staphylococcus aureus* No. 50774 | 5 × 10$^8$ cells/mouse | intravenous | 14 days after infection |
| *Pseudomonas aeruginosa* No. 12 | 2 × 10$^6$ cells/mouse | intra-peritoneal | 7 days after infection |
| *Escherichia coli* P-5101* | 7 × 10$^6$ cells/mouse | intra-peritoneal | 7 days after infection |
| *Candida albicans* 3170 | 0.25 ml of fungal suspension (OD = 1.5) | intravenous | 7 days after infection |

*with 4% mucin

TABLE 2

| | Antiinfectious activity in mice | | | |
|---|---|---|---|---|
| Microorganism | Dose$^a$ (mg/kg) | Compound of Example 15 | | GMP$_4$-A |
| *Staphylococcus aureus* No. 50774 | 12.5 | 13/16$^b$ (81.3) | 23/32 | (71.9) |
| | 3.1 | 15/16 (93.8) | 11/32 | (34.4) |
| | 0.8 | 13/16 (81.3) | 11/32 | (34.4) |
| | 0.2 | 13/16 (81.3) | 6/16 | (37.5) |
| | 0.05 | 9/16 (56.3) | 3/24 | (12.5) |
| | 0.125 | 3/16 (18.8) | 0/8 | (0) |
| | 0$^c$ | 4/32 (12.5) | | |
| *Pseudomonas aeruginosa* No. 12 | 12.5 | 8/8 (100) | 32/48 | (66.7) |
| | 3.1 | 14/16 (87.5) | 27/64 | (42.2) |
| | 0.8 | 14/24 (58.3) | 31/72 | (43.1) |
| | 0.2 | 15/32 (46.9) | 23/56 | (41.1) |
| | 0.05 | 14/32 (43.8) | 16/48 | (33.3) |
| | 0.0125 | 12/32 (37.5) | 12/40 | (30) |
| | 0 | 8/96 (8.3) | | |

TABLE 2-continued

| | Antiinfectious activity in mice | | | | |
|---|---|---|---|---|---|
| Microorganism | Dose[a] (mg/kg) | Compound of Example 15 | | GMP$_4$-A | |
| Escherichia | 50 | 7/8 | (87.5) | 10/16 | (62.5) |
| coli P-5101 | 12.5 | 11/16 | (68.8) | 10/24 | (41.7) |
| | 3.1 | 11/16 | (68.8) | 5/24 | (20.8) |
| | 0.8 | 10/16 | (62.5) | 0/8 | (0) |
| | 0.2 | 7/16 | (43.8) | 0/8 | (0) |
| | 0.05 | 6/16 | (37.5) | — | |
| | 0 | | 2/24 (8.3) | | |
| Candida | 50 | 7/8 | (87.5) | 6/8 | (75) |
| albicans 3170 | 12.5 | 4/8 | (50) | 4/8 | (50) |
| | 3.1 | 4/8 | (50) | 2/8 | (25) |
| | 0.8 | 3/8 | (37.5) | — | |
| | 0 | | 0/8 (0) | | |

[Notes]
[a]Test compounds were intravenously administered once a day 1, 2 and 3 days before infection.
[b]Figures represent (number of survivals)/(number of animals tested) and figures in parenthesis represent percent survival.
[c]The control group to which only physiological saline solution was administered.

(2) Pyrogenicity

Rabbits (each group: three rabbits) were used. Test compounds dissolved in a physiological saline solution were each injected into ear vein of rabbits. The difference between maximum body temperature within three hours after the injection of test compound and the body temperature before the injection was regarded as rise in body temperature. The degree of pyrogenicity was evaluated according to the following criterion: (+): two or more animals showed rise in body temperature of 0.6° C. or more, (±): one animal showed rise in body temperature of 0.6° C. or more, and (−): one animal showed rise in body temperature of 0.6° C. or more. The results are shown in Table 3.

TABLE 3

| | Pyrogenicity in rabbits | | | | |
|---|---|---|---|---|---|
| | Dose (mg/rabbit) | | | | |
| Test compound | 10 | 3 | 1 | 0.3 | 0.1 |
| Compound of Example 15 | + | ± | − | − | − |
| GMP$_4$-A | + | + | + | + | − |

As is clear from the above experimental results in Tables 2 and 3, the compound of Example 15 showed more potent antiinfectious effect and less pyrogenicity than GMP$_4$-A. Thus, the compound of the present invention shows improved properties.

Besides, as to the compounds of Examples 8, 18, 36, 37 and 45 (derivatives of GMP$_3$-A), similar experiments were done. As a result, the compounds of Examples 8 and 18 showed more potent antiinfectious effect and less pyrogenicity than GMP$_3$-A. The pyrogenicity of the compounds of Examples 36, 37 and 45 was by far the less than that of GMP$_3$-A.

(3) Acute toxicity

Male and female ICR mice aged about 6 weeks (each group: 8 mice) were used. The compound of Example 15 was dissolved in distilled water and administered to mice. Mortality was checked for 14 days and LD$_{50}$ was calculated by probit method. The results are shown in Table 4.

TABLE 4

| | Acute toxicity of the compound of Example 15 in mice | |
|---|---|---|
| Route | Sex | LD$_{50}$ (mg/kg) |
| i.v. | male | 292 (261–328*) |
| | female | 266 (237–297) |
| i.p. | male | >600 |
| | female | >600 |
| s.c. | male | >600 |
| | female | >600 |
| p.o. | male | >3000 |
| | female | >3000 |

*Figures in parenthesis represent 95% confidence limits.

The compound of the formula (V) and a pharmaceutically acceptable salt thereof can be used in the prophylaxis and treatment of various microbial infections. They can be administered in oral, parenteral or intrarectal route in the form of a pharmaceutical composition in admixture with conventional carriers. They can be preferably administered in parenteral route in the form of an isotonic aqueous solution, to which a buffering agent and/or solubilizer may be optionally added. Dose of the compounds may vary with kinds of the compounds, administration routes, severity of diseases and age of patients, but is usually in the range of 0.001 to 50 mg/kg/day. These compounds may be administered together with other synthetic antimicrobial agents such as pipemidic acid or nalidixic acid, antibiotics such as gentamicin, carbenicillin, piperacillin, ceftizoxime, or latamoxef, or anticancer agents such as cyclophosphamide, mitomycin C, adriamycin, or bleomycin.

The present invention is illustrated by the following Examples and Reference Examples, but should not be construded to be limited thereto. In these examples, the compounds were identified by elementary analysis, IR spectrum, etc. Rf value was measured by thin layer chromatography with Kieselgel 60F$_{254}$ (manufactured by E. Merck AG, West Germany) using chloroform-methanol-water (15:10:2) as the developing solvent. The optical rotation was measured after 24 hours in methanol unless otherwise specified.

REFERENCE EXAMPLE 1

Preparation of endo-N-acetylmuramidase:

Streptomyces globisporus B-1829 (ATCC 21553) strain was cultivated in a medium (pH 7.5, 70 liters) containing dextrin (2%), defatted soybean meal (0.5%), polypeptone (0.2%), sodium chloride (0.17%), MgSO$_4$ (0.1%), Na$_2$HPO$_4$ (0.5%) and CaCl$_2$ (0.02%), with an aeration rate of 70 liters/minute and a stirring rate of 250 r.p.m. at 30° C. for 3 days. The culture broth was filtered, and to the filtrate (70 liters) was added Amberlite CG-50 (H+ type, manufactured by Rohm and Haas Co., U.S.A., 6.5 kg), and the mixture was stirred for one hour and filtered. The separated resin was eluted with 0.2 M Na$_2$HPO$_4$ (pH 7.5), and the eluate was adjusted to 60% saturation with solid ammonium sulfate. The resulting precipitates were separated by filtration and dissolved in a small amount of deionized water. The solution was applied to a column (3.0×70 cm) of CM-cellulose (Na+ type, manufactured by Bio-Rad Laboratories, U.S.A.) equilibrated with 0.05M phosphate buffer (pH 7.0). The elution was carried out stepwise with 0.05 M and 0.1 M phosphate buffer (pH 7.0). The fraction eluted with 0.1 M phosphate buffer was dialyzed against water and applied to a column (3.0×60 cm) of CM-Sephadex C-25 (Na+ type, manufactured by Pharmacia Fine Chemicals AB, Sweden) equilibrated with 0.05 M phosphate buffer, which was eluted stepwise with 0.05 M and 0.1 M phosphate buffer (pH 7.0). The fraction eluted with 0.1 M phosphate buffer was dialyzed against 0.05 M phosphate buffer (pH 7.0). The dialyzed solution was subjected to gel filtration through Sephadex G-75 (manufactured by Pharmacia, Sweden), and the obtained active fraction was desalted, concentrated and then lyophilized to give endo-N-acetylmuramidase (1,100 mg).

REFERENCE EXAMPLE 2

Preparation of D-alanyl-meso-2,6-diaminopimelic acid endopeptidase:

*Streptomyces globisporus* B-1829 strain was cultivated in a medium (pH 7.5, 70 liters) containing dextrin (2%), defatted soybean meal (0.5%), polypeptone (0.2%), sodium chloride (0.2%), $MgSO_4$ (0.1%), $Na_2HPO_4$ (0.5%), and $CaCl_2$ (0.02%), with an aeration rate of 70 liters/minute and a stirring rate of 250 r.p.m. at 30° C. for 3 days. The culture broth was filtered, and to the filtrate (70 liters) was added Amberlite CG-50 ($H^+$ type, 6.5 kg), and the mixture was stirred for one hour. The resin was separated, washed with water, and then eluted with 0.2 M $Na_2HPO_4$ (pH 7.5) and the eluate was adjusted to 60% saturation with solid ammonium sulfate. The resulting precipitates were separated by filtration and dissolved in a small amount of deionized water and the solution was desalted with an electrodialyzer (SELEMION dialyzing cabinet Type DU-Ob, manufactured by Nippon Rensui Co., Japan) for 2 to 5 hours. The resulting solution was applied to a column (5.0×20 cm) of CM-Sephadex C-25 ($Na^+$ type), which was eluted with a linear gradient at the concentration from 0 to 0.06 M of NaCl. The active fractions were collected, concentrated, subjected to gel filtration through Sephadex G-25 (manufactured by Pharmacia, Sweden) and then lyophilized to give D-alanyl-meso-2,6-diaminopimelic acid endopeptidase (800 mg).

REFERENCE EXAMPLE 3

Immobilization of D-alanyl-meso-2,6-diaminopimelic acid endopeptidase:

D-Alanyl-meso-2,6-diaminopimelic acid endopeptidase (500 mg) obtained in Reference Example 2 was dissolved in 0.05 M phosphate buffer (pH 8.0, 20 ml), and the solution was added to p-aminobenzylcellulose (1,000 mg) which was diazotized in a usual manner, and the mixture was stirred at 4° C. for 20 hours and thereafter was incubated at 37° C. for one hour. After the reaction was finished, the immobilized enzyme was separated by filtration and washed with 0.25 M phosphate buffer (pH 8.0) and water to remove free enzyme. The immobilized enzyme thus obtained was kept at low temperature.

REFERENCE EXAMPLE 4

Preparation of alkali-treated cell walls:

Wet whole cells (520 g) of *Lactobacillus plantarum* ATCC 8014 were suspended in physiological saline (4 liters) and were disrupted with DYNO-Laboratory Mill (manufactured by Shinmaru Enterprises Corporation, Japan). The mixture was centrifuged at 800×g for 10 minutes to remove the undisrupted cells, and to the supernatant was added sodium chloride to give a concentration of 1 M. The cell walls were harvested by a centrifuge (9,000×g, 30 minutes), washed with a large amount of deionized water and collected by centrifugation. This treatment was repeated three times. The washed cell walls were suspended in 0.05 M phosphate buffer (pH 7.0), and thereto was added trypsin (4.2 g), and the mixture was allowed to stand at 37° C. for 6 hours. The reaction mixture was cooled and centrifuged at 800×g for 15 minutes to remove insoluble debris, and the supernatant was further centrifuged at 9,000×g for 30 minutes to collect cell walls. The cell walls were washed with 0.05 M phosphate buffer (pH 7.0) and collected by centrifugation. This treatment was repeated two times to give purified cell walls (86 g).

The purified cell walls (80 g) thus obtained were suspended in 0.1 N NaOH (4.4 liters) and the suspension was stirred at room temperature for 2 hours, neutralized with a concentrated hydrochloric acid and then centrifuged at 9,000×g for 30 minutes to collect cell walls. The cell walls were washed with 1 M NaCl solution and water and then lyophilized to give alkali-treated cell walls (40 g).

REFERENCE EXAMPLE 5

Preparation of $GMP_3$-A and $GMP_4$-A:

The alkali-treated cell walls (1,200 g) of *Lactobacillus plantarum* ATCC 8014 obtained by the method of Reference Example 4 were suspended in a phosphate buffer (pH 8.5, final concentration of 0.02 M; 30 liters) and dispersed well. The suspension was mixed with endo-N-acetylmuramidase (2.4 g), chloroform (50 ml), $CoCl_2.6H_2O$ (14.3 g) and the immobilized D-alanyl-meso-2,6-diaminopimelic acid endopeptidase (1.0 g in dry state) obtained in Reference Example 3 and thereto was added tap water to make total volume of 60 liters. The mixture was stirred at 37° C. for 48 hours. The immobilized enzyme was removed from the reaction mixture with a dehydrator. The resulting solution was adjusted to pH 2.5-3.0 with a concentrated hydrochloric acid, and the resulting precipitates were removed by centrifugation at a high speed. The supernatant was carefully neutralized with a dilute NaOH solution and was passed through a column (10×140 cm) of Diaion PA 316 ($Cl^-$ type, manufactured by Mitsubishi Chemical Industries Co., Ltd., Japan) to remove impurities. The unadsorbed fraction was further applied to a column (14×190 cm) of Diaion PK 212 ($H^+$ type, manufactured by Mitsubishi, Japan), which was eluted with 0.3 M NaCl solution. The eluate was neutralized with a dilute NaOH solution and applied to a column (20×135 cm) of Diaion HP-20 (manufactured by Mitsubishi, Japan), which was eluted with water to give a fraction of $GMP_3$-A and then with 5% methanol to give a fraction of $GMP_4$-A. Each fraction of $GMP_3$-A and $GMP_4$-A thus obtained was desalted and concentrated with a reverse osmosis instrument (RO-Module RT-1, manufactured by Sumitomo Chemical Co., Ltd., Japan), and thereafter, they were each applied to a column (15×135 cm) of CM-Sephadex ($H^+$ type), which was eluted with 0.001 N hydrochloric acid (10 liters). The eluate was neutralized with a dilute NaOH solution, concentrated under reduced pressure below 50° C. and then desalted by gel filtration through a column (6.0×160 cm) of Sephadex G-25. The eluate thus obtained was concentrated under reduced pressure below 50° C. and lyophilized to give $GMP_3$-A and $GMP_4$-A in an amount of 110 g and 90 g, respectively. $[\alpha]_D^{25}$ (c=1.0, water): $GMP_3$-A, −7.8°; $GMP_4$-A, −11.4°.

EXAMPLE 1

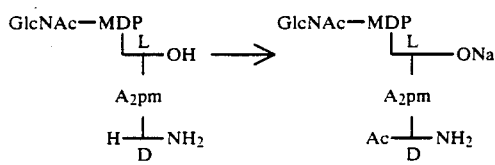

Preparation of sodium β-N-acetyl-glucosaminyl(1→4)-N-acetylmuramyl-L-alanyl-D-isoglutaminyl-(L)-acetyl-(D)-meso-2,6-diaminopimelate-(D)-amide:

To a solution of β-GlcNAc-(1→4)-MurNAc-L-Ala-D-isoGln-(L)-meso-A$_2$pm-(D)-NH$_2$ (5.0 g) in water (80 ml) were added cold aq. saturated NaHCO$_3$ solution (32 ml) and acetic anhydride (32 ml). The resulting foams were suppressed by dropwise addition of diethyl ether. The mixture was allowed to stand overnight at room temperature. The reaction mixture was evaporated to dryness in vacuo. The residue was dissolved in water (25 ml) and applied to a column (5×80 cm) of Sephadex G-25 (manufactured by Pharmacia, Sweden) which was eluted with water. The fractions containing the desired product were collected and concentrated in vacuo. The residue was reprecipitated from methanol-ethyl acetate to give the desired product (4.7 g): mp 187°–196° C. (dec.); Rf: 0.07; $[\alpha]_D^{23} = -0.8°$ (c=0.90).

EXAMPLE 2

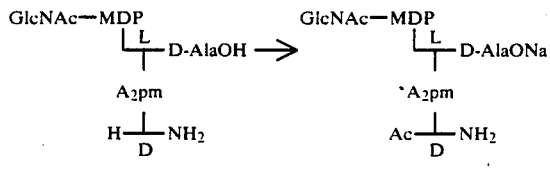

Preparation of sodium β-N-acetyl-glucosaminyl(1→4)-N-acetylmuramyl-L-alanyl-D-isoglutaminyl-(L)-acetyl-(D)-meso-2,6-diaminopimelic acid-(D)-amide-(L)-D-alanate:

The title compound was prepared from β-GlcNAc-(1→4)-MurNAc-L-Ala-D-isoGln-(L)-meso-A$_2$pm-(D)-NH$_2$-(L)-D-AlaOH in substantially the same manner as in Example 1: mp 188°–191° C. (dec.); Rf: 0.06; $[\alpha]_D^{23} = -6.8°$ (c=0.97).

REFERENCE EXAMPLE 6

Preparation of an N-hydroxysuccinimide ester of a carboxylic acid:

To a solution of a carboxylic acid (1 mmol) in ethyl acetate (10 ml) were added N-hydroxysuccinimide (1.2 mmol) and dicyclohexylcarbodiimide (1.2 mmol) and the mixture was stirred overnight. The resulting precipitate of N,N'-dicyclohexylurea was removed by filtration and the filtrate was evaporated in vacuo. The residue was applied to a column of silica gel which was eluted with chloroform. The fractions containing the desired product were collected and concentrated in vacuo to give the N-hydroxysuccinimide ester of the carboxylic acid. In the cases of stearic acid and docosanoic acid, a mixture of tetrahydrofuran and ethyl acetate was used as the reaction solvent.

EXAMPLE 3

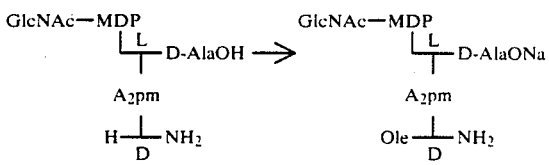

Preparation of sodium β-N-acetyl-glucosaminyl(1→4)-N-acetylmuramyl-L-alanyl-D-isoglutaminyl-(L)-oleoyl-(D)-meso-2,6-diaminopimelic acid-(D)-amide-(L)-D-alanate:

β-GlcNAc-(1→4)-MurNAc-L-Ala-D-isoGln-(L)-meso-A$_2$pm-(D)-NH$_2$-(L)-D-AlaOH (1.0 g) was suspended in dimethylformamide (20 ml), and N-oleoyloxysuccinimide (600 mg) and triethylamine (0.3 ml) were added. The mixture was stirred overnight at room temperature. Ethyl acetate was added to the reaction mixture to give colorless precipitate, which was collected by filtration and dissolved in water (50 ml). The solution was passed through a column (2.5×30 cm) of CM-Sephadex C-25 (H$^+$ type, manufactured by Pharmacia, Sweden). The combined eluate was adjusted to pH 7.0 with NaOH solution and concentrated in vacuo. The residue was dissolved in methanol and applied to a column (2.5×80 cm) of Sephadex LH-20 (manufactured by Pharmacia, Sweden) which was eluted with methanol. The fractions containing the desired product were collected, and the solvent was evaporated off in vacuo. Ethyl acetate was added to the residue. The resulting precipitate was collected by filtration to give the desired product (805 mg): mp 183°–185° C. (dec.); Rf: 0.42; $[\alpha]_D^{23} = -9.6°$ (c=0.96).

EXAMPLES 4 to 14

The compounds showh in Table 5 were prepared from the corresponding starting materials in substantially the same manner as in Example 3. All compounds in the table melted with decomposition.

TABLE 5

GlcNAc—MDP
└L┬Y
A$_2$pm
R$_1$CO—│—NH$_2$
     D

| Ex. | R$_1$ | Y | mp (°C.) | Rf | $[\alpha]_D^*$ (c) |
|---|---|---|---|---|---|
| 4 | CH$_3$(CH$_2$)$_3$CH(C$_2$H$_5$)— | ONa | 183–185 | 0.32 | +8.6° (0.47) |
| 5 | CH$_3$(CH$_2$)$_8$— | " | 180–185 | 0.30 | +5.1° (0.37) |
| 6 | CH$_3$(CH$_2$)$_{10}$— | " | 180–183 | 0.41 | +5.7° (0.98) |
| 7 | CH$_3$(CH$_2$)$_{12}$— | " | 177–181 | 0.35 | +5.8° (0.97) |
| 8 | CH$_3$(CH$_2$)$_7$CH=CH(CH$_2$)$_7$— | " | 175–185 | 0.39 | +5.1° (0.90) |

TABLE 5-continued

GlcNAc—MDP
$$\underset{\text{A}_2\text{pm}}{\overset{\text{L}}{\vdash}}\text{Y}$$
$$R_1CO\underset{D}{\vdash}NH_2$$

| Ex. | R$_1$ | Y | mp (°C.) | Rf | [α]$_D$* (c) |
|---|---|---|---|---|---|
| 9 | CH$_3$(CH$_2$)$_4$CH=CHCH$_2$—(CH$_2$)$_7$CH=CH | " | 171–177 | 0.42 | +0.4° (0.56) |
| 10 | CH$_3$(CH$_2$)$_3$CH(C$_2$H$_5$)— | D-AlaONa | 186–188 | 0.30 | −3.5° (0.55) |
| 11 | CH$_3$(CH$_2$)$_8$— | " | 175–177 | 0.36 | −6.1° (0.55) |
| 12 | CH$_3$(CH$_2$)$_{10}$— | " | 180–184 | 0.40 | −8.6° (0.90) |
| 13 | CH$_3$(CH$_2$)$_{12}$— | " | 177–180 | 0.45 | −9.7° (0.98) |
| 14 | CH$_3$(CH$_2$)$_4$CH=CHCH$_2$—(CH$_2$)$_7$CH=CH | " | 175–178 | 0.43 | −6.0° (0.92) |

*at 23–25° C.

EXAMPLE 15

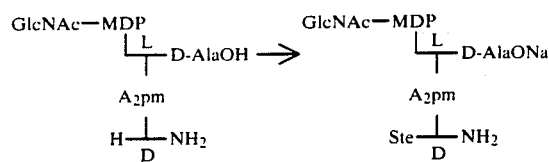

Preparation of sodium β-N-acetylglucosaminyl(1→4)-N-acetylmuramyl-L-alanyl-D-isoglutaminyl-(L)-stearoyl-(D)-meso-2,6-diaminopimelic acid-(D)-amide(L)- D-alanate:

β-GlcNAc-(1→4)-MurNAc-L-Ala-D-isoGln-(L)-meso-A$_2$pm-(D)-NH$_2$-(L)-D-AlaOH (500 mg) was suspended in dimethylformamide (10 ml), and N-stearoyloxysuccinimide (300 mg) and NaOH (23.1 mg) were added. The mixture was stirred overnight at room temperature. Ethyl acetate was added to the reaction mixture to give colorless precipitate, which was collected by filtration and dissolved in water (10 ml). The solution was passed through a column (3×80 cm) of SP-Sephadex C-25 (Na+ type, manufactured by Pharmacia, Sweden). The collected eluate was adjusted to pH 7.0 with NaOH solution and concentrated in vacuo. The residue was dissolved in methanol (10 ml) and applied to a column (2.5×80 cm) of Sephadex LH-20 which was eluted with methanol. The fractions containing the desired product were collected, and the solvent was evaporated off in vacuo. Ethyl acetate was added to the residue. The resulting precipitate was collected by filtration to give the desired product (507 mg): mp 184°–188° C. (dec.); Rf: 0.44; [α]$_D^{23}$= −7.3° (c=0.48).

EXAMPLE 16

Preparation of β-N-acetylglucosaminyl-(1→4)-N-acetylmuramyl-L-alanyl-D-isoglutaminyl-(L)-stearoyl-(D)-meso-2,6-diaminopimelic acid-(D)-amide-(L)-D-alanine:

β-GlcNAc-(1→4)-MurNAc-L-Ala-D-isoGln-(L)-Ste(D)-meso-A$_2$pm-(D)-NH$_2$-(L)-D-AlaONa (500 mg) obtained in Example 15 was dissolved in water saturated with butanol (200 ml). The solution was passed through a column (2.5×4.5 cm) of Dowex 50W×8 (100–200 mesh, H+ type, manufactured by The Dow Chemical Company, U.S.A.) which was eluted with the same solvent. The fractions containing the desired product were collected, and the solvent was evaporated off in vacuo. The residue was suspended in a small amount of ethanol and triturated with ethyl acetate to give the desired product (438 mg): mp 198°–205° C. (dec.); Rf: 0.44.

EXAMPLES 17 to 21

The compounds shown in Table 6 were prepared from the corresponding starting materials in substantially the same manner as in Example 15. All compounds in the table melted with decomposition.

TABLE 6

GlcNAc—MDP
$$\underset{\text{A}_2\text{pm}}{\overset{\text{L}}{\vdash}}\text{Y}$$
$$R_1CO\underset{D}{\vdash}NH_2$$

| Example | R$_1$ | Y | mp (°C.) | Rf | [α]$_D$* (c) |
|---|---|---|---|---|---|
| 17 | CH$_3$(CH$_2$)$_{14}$— | ONa | 180–185 | 0.42 | +4.3° (0.45) |
| 18 | CH$_3$(CH$_2$)$_{16}$— | " | 185–190 | 0.38 | +4.7° (1.05) |
| 19 | CH$_3$(CH$_2$)$_{20}$— | " | 173–177 | 0.50 | +1.4° (0.47) |
| 20 | CH$_3$(CH$_2$)$_{14}$— | D-AlaONa | 186–188 | 0.43 | −8.4° (0.44) |
| 21 | CH$_3$(CH$_2$)$_{20}$— | " | 189–192 | 0.50 | +1.8° (0.15)** |

*at 23–28° C.
**in water

EXAMPLE 22

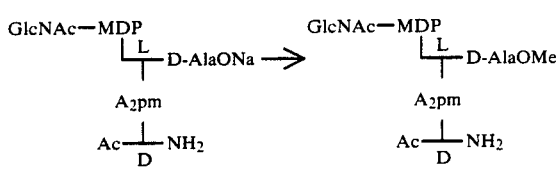

Preparation of β-N-acetylglucosaminyl-(1→4)-N-acetylmuramyl-L-alanyl-D-isoglutaminyl-(L)-acetyl-(D)-meso-2,6-diaminopimelic acid-(D)-amide-(L)-D-alanine methyl ester:

To a solution of β-GlcNAc-(1→4)-MurNAc-L-Ala-D-isoGln-(L)-Ac-(D)-meso-A₂pm-(D)-NH₂-(L)-D-AlaONa (obtained in Example 2) (500 mg) in dried methanol (15 ml) was added methyl iodide (5 ml) and the mixture was stirred for 4 days at room temperature. The reaction mixture was evaporated in vacuo and the residue was dissolved in water (10 ml). The solution was passed through a column (2.5×80 cm) of DEAE-Sephadex A-25 (Cl⁻ type, manufactured by Pharmacia, Sweden) which was eluted with water. The fractions containing the desired product were combined and concentrated in vacuo. The residue was dissolved in methanol (5 ml) and applied to a column (2.5×80 cm) of Sephadex LH-20 which was eluted with methanol. The fractions containing the desired product were collected and the solvent was evaporated off in vacuo. Ethyl acetate was added to the residue. The resulting precipitate was collected by filtration to give the desired product (361 mg): mp 157°–168° C. (dec.); Rf: 0.25; $[\alpha]_D^{25} = -1.6°$ (c=0.45).

EXAMPLE 23

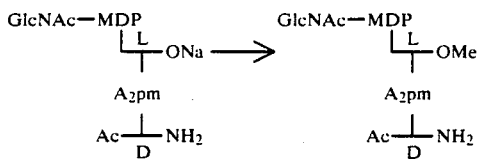

Preparation of β-N-acetylglucosaminyl-(1→4)-N-acetylmuramyl-L-alanyl-D-isoglutaminyl-(L)-acetyl-(D)-meso-2,6-diaminopimelic acid-(D)-amide-(L)-methyl ester:

The title compound was prepared from β-GlcNAc(1→4)-MurNAc-L-Ala-D-isoGln-(L)-Ac-(D)-meso-A₂pm-(D)-NH₂(L)-ONa in substantially the same manner as in Example 22: mp 154°–164° C. (dec.); Rf: 0.25; $[\alpha]_D^{25} = -1.0°$ (c=0.46).

REFERENCE EXAMPLE 7

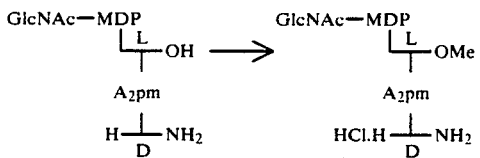

Preparation of β-N-acetylglucosaminyl-(1→4)-N-acetylmuramyl-L-alanyl-D-isoglutaminyl-(L)-meso-2,6-diaminopimelic acid-(D)-amide-(L)-methyl ester hydrochloride:

β-GlcNAc-(1→4)-MurNAc-L-Ala-D-isoGln-(L)-meso-A₂pm-(D)-NH₂ (500 mg) was dissolved in 0.05N HCl-MeOH (10 ml) and allowed to stand for 5 days at room temperature. Ethyl acetate was added to the reaction mixture. The resulting precipitate was collected by filtration and dissolved in water (5 ml). The solution was passed through a column (2.5×80 cm) of QAE-Sephadex A-25 (Cl⁻ type, manufactured by Pharmacia, Sweden) which was eluted with water. The fractions containing the desired product were collected and concentrated in vacuo. The residue was dissolved in methanol (5 ml) and applied to a column (2.5×80 cm) of Sephadex LH-20 which was eluted with methanol. The fractions containing the desired product were collected and the solvent was evaporated off in vacuo. Ethyl acetate was added to the residue. The resulting precipitate was collected by filtration to give the desired product (410 mg); mp 150°–169° C. (dec.); Rf: 0.05; $[\alpha]_D^{25} = -11.8°$ (c=0.43).

REFERENCE EXAMPLE 8

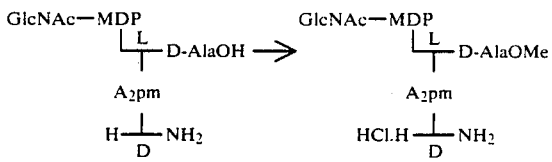

Preparation of β-N-acetylglucosaminyl-(1→4)-N-acetylmuramyl-L-alanyl-D-isoglutaminyl-(L)-meso-2,6-diaminopimelic acid-(D)-amide-(L)-D-alanine methyl ester hydrochloride:

The title compound was prepared from β-GlcNAc-(1→4)-MurNAc-L-Ala-D-isoGln-(L)-meso-A₂pm-(D)-NH₂-(L)-D-AlaOH in substantially the same manner as in Reference Example 7: mp 173°–177° C. (dec.); Rf: 0.05; $[\alpha]_D^{25} = -6.0°$ (c=0.39).

EXAMPLE 24

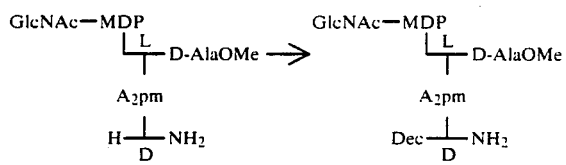

Preparation of β-N-acetylglucosaminyl-(1→4)-N-acetylmuramyl-L-alanyl-D-isoglutaminyl-(L)-decanoyl-(D)-meso-2,6-diaminopimelic acid-(D)-amide-(L)-D-alanine methyl ester:

The title compound was prepared from β-GlcNAc-(1→4)-MurNAc-L-Ala-D-isoGln-(L)-meso-A₂pm-(D)-NH₂-(L)-D-AlaOMe and N-decanoyloxysuccinimide in substantially the same manner as in Example 15: mp 150°–152° C. (dec.); Rf: 0.62; $[\alpha]_D^{25} = +2.9°$ (c=0.45, H₂O)

EXAMPLE 25

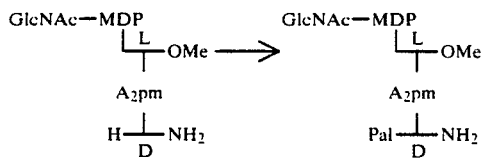

Preparation of β-N-acetylglucosaminyl-(1→4)-N-acetylmuramyl-L-alanyl-D-isoglutaminyl-(L)-palmitoyl-(D)-meso-2,6-diaminopimelic acid-(D)-amide-(L)-methyl ester:

The title compound was prepared from β-GlcNAc-(1→4)-MurNAc-L-Ala-D-isoGln-(L)-meso-A₂pm-(D)-NH₂-(L)-OMe and N-palmitoyloxysuccinimide in substantially the same manner as in Example 15: mp 160°–175° C. (dec.); Rf: 0.66; $[\alpha]_D^{25} = -3.6°$ (c=0.18).

EXAMPLE 26

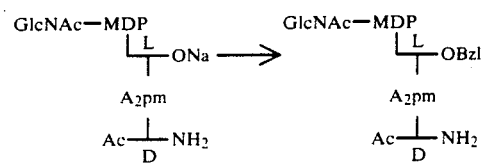

Preparation of β-N-acetylglucosaminyl-(1→4)-N-acetylmuramyl-L-alanyl-D-isoglutaminyl-(L)-acetyl-(D)-meso-2,6-diaminopimelic acid-(D)-amide-(L)-benzyl ester:

The title compound was prepared from β-GlcNAc-(1→4)-MurNAc-L-Ala-D-isoGln-(L)-Ac-(D)-meso-A$_2$pm-(D)-NH$_2$-(L)-ONa, benzyl bromide and dried dimethylformamide in substantially the same manner as in Example 22: mp 150°–155° C. (dec.); Rf: 0.41; $[α]_D^{25} = -1.6°$ (c=0.52).

EXAMPLE 27

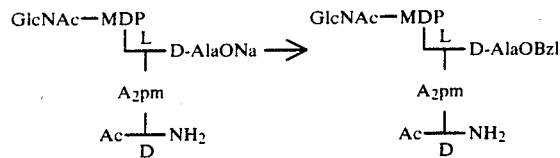

Preparation of β-N-acetylglucosaminyl-(1→4)-N-acetylmuramyl-L-alanyl-D-isoglutaminyl-(L)-acetyl-(D)-meso-2,6-diaminopimelic acid-(D)-amide-(L)-D-alanine benzyl ester:

The title compound was prepared from β-GlcNAc-(1→4)-MurNAc-L-Ala-D-isoGln-(L)-Ac-(D)-meso-A$_2$pm-(D)-NH$_2$-(L)-D-AlaONa, benzyl bromide and dried dimethylformamide in substantially the same manner as in Example 22: mp 172°–193° C. (dec.); Rf: 0.41; $[α]_D^{25} = -2.7°$ (c=0.53, H$_2$O)

EXAMPLE 28

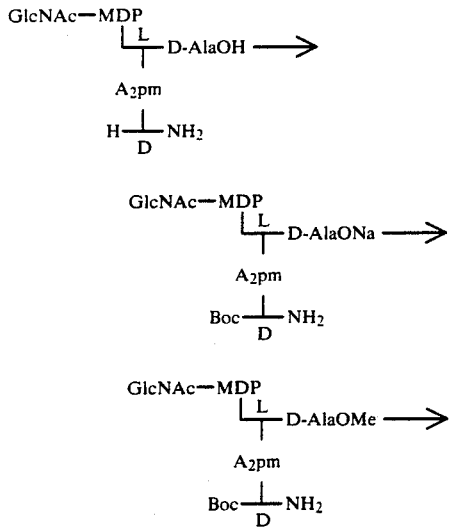

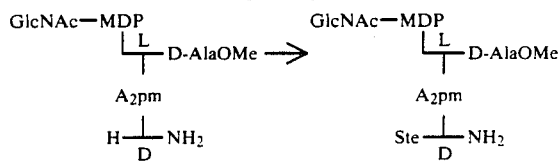

Preparation of β-N-acetylglucosaminyl-(1→4)-N-acetylmuramyl-L-alanyl-D-isoglutaminyl-(L)-stearoyl-(D)-meso-2,6-diaminopimelic acid-(D)-amide-(L)-D-alanine methyl ester:

β-GlcNAc-(1→4)-MurNAc-L-Ala-D-isoGln-(L)-meso-A$_2$pm-(D)-NH$_2$-(L)-D-AlaOH (2.12 g) was suspended in dimethylformamide (10 ml), and S-t-butoxycarbonyl-4,6-dimethyl-2-mercaptopyrimidine (1.17 g) was added thereto. The mixture was stirred for 5 days at room temperature. Ethyl acetate was added to the reaction mixture. The resulting precipitate was collected by filtration and dissolved in water (50 ml). The solution was passed through a column (2.5×10 cm) of Dowex 50 W×8 (H$^+$type) which was eluted with water. The collected eluate was adjusted to pH 7.0 with NaOH solution and concentrated in vacuo. The residue was dissolved in a small amount of methanol and triturated with ethyl acetate to give β-GlcNAc-(1→4)-MurNAc-L-Ala-D-isoGln-(L)-Boc-(D)-meso-A$_2$pm-(D)-NH$_2$-(L)-D-AlaONa asS colorless powder. This product was dissolved in dried dimethylformamide (10 ml) and methyl iodide (5 ml) was added. The mixture was stirred for 4 days at room temperature. Ethyl acetate was added to the reaction mixture and the resulting precipitate was collected by filtration. The precipitate was dissolved in CHCl$_3$-EtOH-H$_2$O (15:12:2) (20 ml) and applied to a column (2.5×30 cm) of Kieselgel 60 (70–200 mesh, manufactured by E. Merck AG, West Germany) which was eluted with the same solvent system. The fractions containing β-GlcNAc-(1→4)-MurNAc-L-Ala-D-isoGln-(L)-Boc-(D)-meso-A$_2$pm-(D)-NH$_2$-(L)-D-AlaOMe were collected and the solvent was evaporated off in vacuo. This product was dissolved in trifluoroacetic acid (5 ml) and anisole (0.5 ml) at 0° C. After stirring for 2 hours at 0° C., the reaction mixture was evaporated in vacuo. A solution of the residual β-GlcNAc-(1→4)-MurNAc-L-Ala-D-isoGln-(L)-meso-A$_2$pm-(D)-NH$_2$-(L)-D-AlaOMe trifluoroacetate (1.07 g) thus obtained, N-stearoyloxysuccinimide (535 mg) and N-methylmorpholine (0.4 ml) in dimethylformamide (20 ml) was stirred overnight at room temperature. Ethyl acetate was added to the reaction mixture to give colorless precipitate, which was collected by filtration. The precipitate was dissolved in CHCl$_3$-EtOH-H$_2$O (15:12:2) (20 ml) and applied to a column (2.5×30 cm) of Kieselgel 60 (70–200 mesh) which was eluted with the same solvent system. The fractions containing βGlcNAc-(1→4)-MurNAc-L-Ala-D-isoGln-(L)-Ste-(D)-meso-A$_2$pm-(D)-NH$_2$-(L)-D-AlaOMe were collected and the solvent was evaporated off in vacuo. The residue was dissolved in CHCl$_3$-EtOH-H$_2$O (15:12:2) (20 ml) and applied to a column (2.5×80 cm) of Sephadex LH-20 which was eluted with the same solvent system. The fractions containing the desired product were collected and concentrated in vacuo, which was dissolved in ethanol and triturated with ethyl acetate to give the desired product (634 mg): mp 170°–185° C. (dec.); Rf: 0.73.

EXAMPLE 29 TO 31

The compounds shown in Table 7 were prepared in substantially the same manner as in Example 28, using the corresponding alkyl or benzyl bromide.

TABLE 7

GlcNAc—MDP
└L┬D-AlaOR
A₂pm
Ste─┬─NH₂
    D

| Example | R | mp (°C.) | Rf |
|---|---|---|---|
| 29 | CH₂CH₃ | 175–190 (dec.) | 0.77 |
| 30 | (CH₂)₃CH₃ | 162–168 (dec.) | 0.79 |
| 31 | CH₂C₆H₅ | 173–200 (dec.) | 0.82 |

EXAMPLE 32

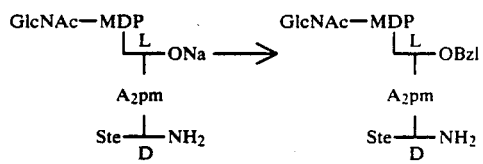

Preparation of β-N-acetylglucosaminyl-(1→4)-N-acetylmuramyl-L-alanyl-D-isoglutaminyl-(L)-stearoyl-(D)-meso-2,6-diaminopimelic acid-(D)-amide-(L)-benzyl ester:

β-GlcNAc-(1→4)-MurNAc-L-Ala-D-isoGln-(L)-Ste-(D)-meso-A₂pm-(D)-NH₂-(L)-ONa (2.0 g) obtained in Example 18 was dissolved in dimethylformamide (20 ml) and benzyl bromide (2 ml) was added. The mixture was allowed to stand for 5 days at room temperature. Ethyl acetate was added to the reaction mixture to give precipitate, which was collected by filtration. The precipitate was dissolved in CHCl₃-EtOH-H₂O (15:12:2) (20 ml) and applied to a column (2.5×30 cm) of Kieselgel 60 (70–200 mesh) which was eluted with the same solvent system. The fractions containing the desired product were collected and the solvent was evaporated off in vacuo. The residue was dissolved in CHCl₃-EtOH-H₂O (15:12:2) (20 ml) and applied to a column (2.5×80 cm) of Sephadex LH-20 which was eluted with the same solvent system. The fractions containing the desired product were collected and concentrated in vacuo. The residue was dissolved in ethanol and triturated with ethyl acetate to give the desired product (1.3 g): mp 183°–188° C. (dec.); Rf: 0.80.

EXAMPLES 33 TO 35

The compounds shown in Table 8 were prepared from β-GlcNAc-(1→4)-MurNAc-L-Ala-D-isoGln-(L)-Ste-(D)-meso-A₂pm-(D)-NH₂-(L)-ONa and the corresponding alkyl halides in substantially the same manner as in Example 32.

TABLE 8

GlcNAc—MDP
└L┬OR
A₂pm
Ste─┬─NH₂
    D

| Example | R | mp (°C.) | Rf |
|---|---|---|---|
| 33 | CH₃ | 160–170 (dec.) | 0.73 |
| 34 | CH₂CH₃ | 149–155 (dec.) | 0.77 |
| 35 | (CH₂)₃CH₃ | 150–157 (dec.) | 0.79 |

EXAMPLE 36

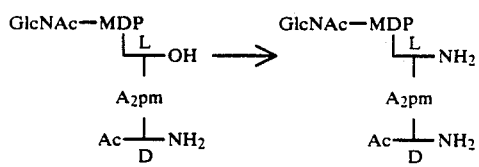

Preparation of β-N-acetylglucosaminyl-(1→4)-N-acetylmuramyl-L-alanyl-D-isoglutaminyl-(L)-acetyl-(D)-meso-2,6-diaminopimelic acid-(D),(L)-diamide:

β-GlcNAc-(1→4)-MurNAc-L-Ala-D-isoGln-(L)-Ac-(D)-Meso-A₂pm-(D)-NH₂-(L)-ONa (454 mg) obtained in Example 1 was dissolved in water (100 ml) and applied to a column (2.5×30 cm) of DEAE-Sephadex A-25 (CH₃COO⁻ type). The column was washed with water and eluted with 2 N AcOH. The fractions containing β-GlcNAc-(1→4)-MurNAc-L-Ala-D-isoGln-(L)-Ac-(D)-meso-A₂pm-(D)-NH₂ were collected and concentrated in vacuo. The residue was dissolved in a small amount of dimethylformamide and triturated with ethyl acetate to give precipitate, which was collected by filtration. A solution of the precipitate thus obtained, N-hydroxysuccinimide (58 mg) and dicyclohexylcarbodiimide (103 mg) in dried dimethylformamide (5 ml) was stirred overnight at room temperature. After the resulting precipitate of N,N'-dicyclohexylurea was removed by filtration, 2.8% ammonia water (0.6 ml) was added to the filtrate. The mixture was stirred overnight at room temperature and concentrated in vacuo. To the concentrate was added ethyl acetate to give precipitate. The precipitate was collected by filtration and dissolved in water (10 ml). The solution was passed through a column (2.5×80 cm) of DEAE-Sephadex A-25 (Cl⁻ type), followed by rechromatography on a column (2.5×80 cm) of SP-Sephadex C-25 (Na⁺ type). The fractions containing the desired product were collected and concentrated in vacuo. The residue was dissolved in methanol (5 ml) and applied to a column (2.5×80 cm) of Sephadex LH-20. The fractions containing the desired product were collected and the solvent was evaporated off in vacuo. Ethyl acetate was added to the residue. The resulting precipitate was collected by filtration to give the desired product (326 mg): mp 167°–171° C. (dec.); Rf: 0.08; $[\alpha]_D^{23} = +2.3°$ (C=1.03).

EXAMPLES 37 TO 43

The compounds shown in Table 9 were prepared from the corresponding starting materials and alkylamines in substantially the same manner as in Example 36. All compounds in the table melted with decomposition.

TABLE 9

$$\begin{array}{c} \text{GlcNAc—MDP} \\ \overset{L}{\underset{|}{\vdash}}\text{Y} \\ \text{A}_2\text{pm} \\ \text{R}_1\text{CO}\overset{|}{\underset{D}{\vdash}}\text{NH}_2 \end{array}$$

| Example | $R_1$ | Y | mp (°C.) | Rf | $[\alpha]_D^*$ (c) |
|---------|-------|---|----------|-----|-------------------|
| 37 | $CH_3$— | $NH(CH_2)_9CH_3$ | 155–164 | 0.50 | +0.4° (0.56) |
| 38 | $CH_3$— | $NH(CH_2)_{11}CH_3$ | 157–165 | 0.51 | +1.0° (1.01) |
| 39 | $CH_3(CH_2)_8$— | $NH_2$ | 159–165 | 0.42 | +0.5° (0.45) |
| 40 | $CH_3(CH_2)_7CH$<br>$\parallel$<br>$—(CH_2)_7CH$ | $NH_2$ | 165–172 | 0.62 | +1.5° (0.90) |
| 41 | $CH_3$— | D-AlaNH$_2$ | 173–180 | 0.10 | −1.3° (1.00) |
| 42 | $CH_3$— | D-AlaNH(CH$_2$)$_9$CH$_3$ | 156–164 | 0.49 | −2.0° (0.51)** |
| 43 | $CH_3$— | D-AlaNH(CH$_2$)$_{11}$CH$_3$ | 199–210 | 0.49 | +1.1° (0.15)** |

*at 23–28° C.
**in water

EXAMPLE 44

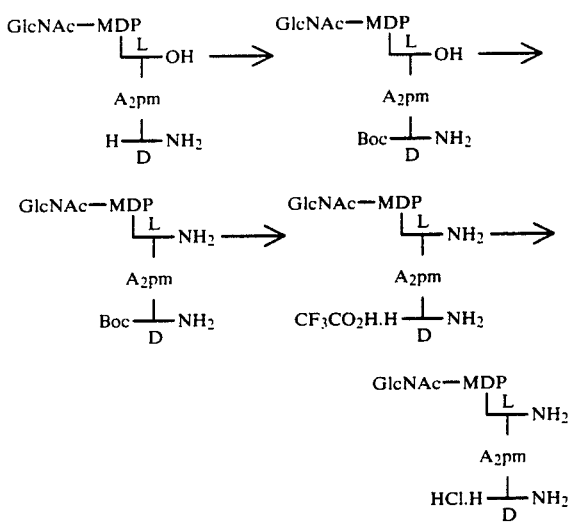

Preparation of β-N-acetylglucosaminyl-(1→4)-N-acetylmuramyl-L-alanyl-D-isoglutaminyl-(L)-meso-2,6-diaminopimelic acid-(D),(L)-diamide hydrochloride:

β-GlcNAc-(1→4)-MurNAc-L-Ala-D-isoGln-(L)-meso-A$_2$pm-(D)-NH$_2$ (5.0 g) was suspended in dimethylformamide (25 ml), and S-t-butoxycarbonyl-4,6-dimethyl-2-mercaptopyrimidine (1.5 g) was added. The mixture was stirred for 4 days at room temperature. Ethyl acetate was added to the reaction mixture to give precipitate, which was collected by filtration and dissolved in water (100 ml). The solution was passed through a column (5×50 cm) of CM-Sephadex C-25 (H+ type) which was eluted with water. The collected eluate was concentrated in vacuo. The residue was dissolved in a small amount of dimethylformamide and triturated with ethyl acetate to give β-GlcNAc-(1→4)-MurNAc-L-Ala-D-isoGln-(L)-Boc-(D)-meso-A$_2$pm-(D)-NH$_2$ (2.0 g). This product was dissolved in dried dimethylformamide (20 ml), and N-hydroxysuccinimide (280 mg) and dicyclohexylcarbodiimide (500 mg) were added. The mixture was stirred overnight at room temperature. After the resulting precipitate of N,N'-dicyclohexylurea was removed by filtration, 2.8 % ammonia water (2.4 ml) was added to the filtrate. The solution was stirred overnight at room temperature and concentrated in vacuo. Ethyl acetate was added to the residue to give precipitate, which was collected by filtration. The precipitate of β-GlcNAc-(1→4)-MurNAc-L-Ala-D-isoGln-(L)-Boc-(D)-meso-A$_2$pm-(D), (L)-diNH$_2$ was dissolved in trifluoroacetic acid (10 ml) and anisole (2 ml) at 0° C. After stirring for 4 hours at 0° C., the reaction mixture was evaporated in vacuo. Ethyl acetate was added to the residue to give precipitate, which was collected by filtration. The precipitate of β-GlcNAc-(1→4)-MurNAc-L-Ala-D-isoGln-(L)-meso-A$_2$pm-(D),(L)-diNH$_2$ trifluoroacetate was dissolved in water (200 ml) and applied to a column ( 3×50 cm) of CM-Sephadex C-25 (H+ type), which was washed with water and then eluted with 0.01 N HCl. The fractions containing the desired product were collected, adjusted to pH 7 with NaOH solution and concentrated in vacuo. The residue was dissolved in methanol (5 ml) and applied to a column (2.5×80 cm) of Sephadex LH-20 which was eluted with methanol. The fractions containing the desired product were collected and the solvent was evaporated off in vacuo. Ethyl acetate was added to the residue. The resulting precipitate was collected by filtration to give the desired product (1.25 g): mp 183°–198° C. (dec.); Rf: 0.01; $[\alpha]_D^{26}$= −3.4° (c=0.92).

EXAMPLE 45

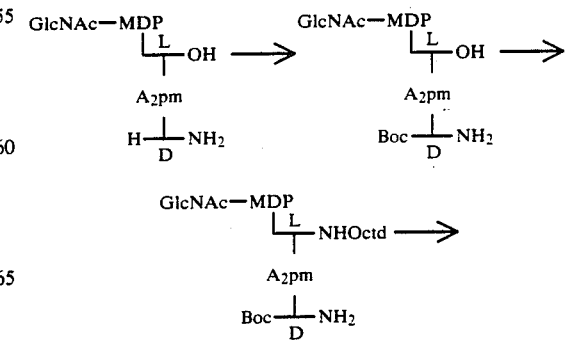

-continued

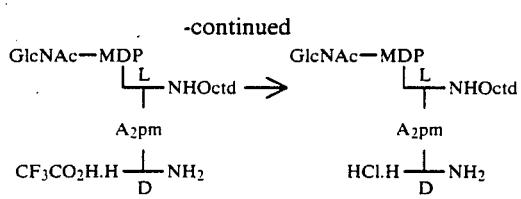

CF$_3$CO$_2$H.H—|—NH$_2$      HCl.H—|—NH$_2$
          D                     D

Preparation of β-N-acetylglucosaminyl-(1→4)-N-acetylmuramyl-L-alanyl-D-isoglutaminyl-(L)-meso-2,6-diaminopimelic acid-(D)-amide-(L)-octadecylamide hydrochloride:

The title compound was prepared in substantially the same manner as in Example 44, using octadecylamine: mp. 189°–195° C. (dec.); Rf: 0.23; [β]$_D^{25}$ = −6.7° (c=0.96).

What is claimed:

1. A compound of the formula:

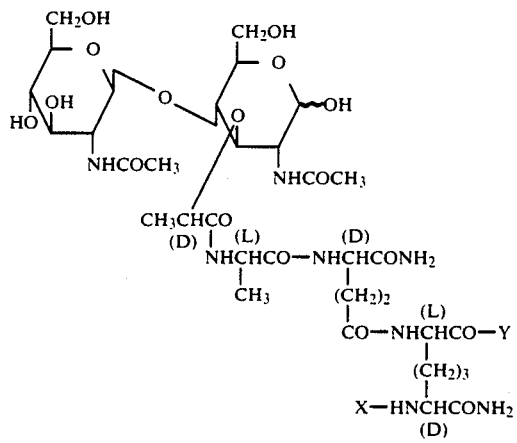

wherein X is hydrogen or a group of the formula: R$_1$CO—, Y is hydroxy or a group of the formula: —OR$_2$, —NH—R$_3$ or

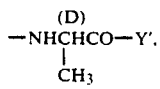

R$_1$ is C$_{1-30}$ alkyl or C$_{2-30}$ alkenyl, R$_2$ is C$_{1-4}$ alkyl or benzyl, R$_3$ is hydrogen or C$_{1-30}$ alkyl, Y' is hydroxy or a group of the formula: —OR$_2$ or —NH—R$_3$, (D) and (L) mean the configuration, provided that when X is hydrogen, Y is a group of the formula: —NH—R$_3$, or

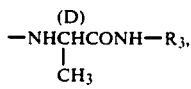

wherein R$_3'$ is C$_{1-30}$ alkyl, or a pharmaceutically acceptable salt thereof.

2. A compound according to claim 1, wherein X is a group of the formula: R$_1$CO— wherein R$_1$ is a straight alkyl group having 1 to 21 carbon atoms or a straight alkenyl group having 1 to 2 double bonds and having 2 to 21 carbon atoms; and Y is hydroxy group, an alkoxy group having 1 to 4 carbon atoms, benzyloxy group, amino group, an amino group mono-substituted by a straight alkyl group having 1 to 21 atoms, or a group of the formula:

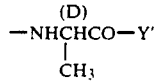

wherein Y' is hydroxy group, an alkoxy group having 1 to 4 carbon atoms, benzyloxy group, amino group, or an amino group mono-substituted by a straight alkyl group having 1 to 21 carbon atoms, or a pharmaceutically acceptable salt thereof.

3. A compound according to claim 1, wherein X is hydrogen atom; and Y is an amino group mono-substituted by a straight alkyl group having 1 to 21 carbon atoms, or a group of the formula:

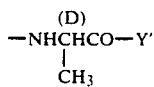

wherein Y' is an amino group mono-substituted by a straight alkyl group having 1 to 21 carbon atoms, or a pharmaceutically acceptable salt thereof.

4. A compound according to claim 1, wherein X is a group of the formula: R$_1$CO— wherein R$_1$ is a straight alkyl group having 11 to 17 carbon atoms or a straight alkenyl group having 1 to 2 double bonds and having 11 to 17 carbon atoms, and Y is hydroxy group, an alkoxy group having 1 to 4 carbon atoms or benzyloxy group, or a pharmaceutically acceptable salt thereof.

5. A compound according to claim 1, wherein X is a group of the formula: R$_1$CO— wherein R$_1$ is a straight alkyl group having 11 to 17 carbon atoms, and Y is a group of the formula:

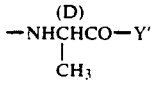

wherein Y' is hydroxy group, an alkoxy group having 1 to 4 carbon atoms or benzyloxy group, or a pharmaceutically acceptable salt thereof.

6. A compound according to claim 1, wherein X is hydrogen atom or a group of the formula: R$_1$CO— wherein R$_1$ is a straight alkyl group having 1 to 4 carbon atoms, and Y is an amino group mono-substituted by a straight alkyl group having 1 to 21 carbon atoms, or a pharmaceutically acceptable salt thereof.

7. A compound according to claim 1, wherein X is a group of the formula: R$_1$CO— wherein R$_1$ is a straight alkyl group having 11 to 17 carbon atoms or a straight alkenyl group having 1 to 2 double bonds and having 11 to 17 carbon atoms, and Y is amino group or an amino group mono-substituted by a straight alkyl group having 1 to 4 carbon atoms.

8. A compound according to claim 1, wherein X is stearoyl or palmitoyl group, and Y is a group of the formula:

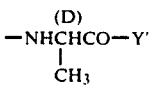

wherein Y' is hydroxy group, a straight alkoxy group having 1 to 4 carbon atoms or benzyloxy group, or a pharmaceutically acceptable salt thereof.

9. The compound according to claim 8, wherein X is palmitoyl group, and Y is a group of the formula:

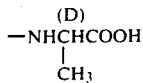

or a pharmaceutically acceptable salt thereof.

10. The compound according to claim 8, wherein X is stearoyl group, and Y is a group of the formula:

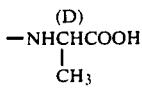

or a pharmaceutically acceptable salt thereof.

11. A compound according to claim 10, which is in the form of sodium salt.

12. A compound according to claim 1, wherein X is hydrogen atom or acetyl group, and Y is an amino group mono-substituted by a straight alkyl group having 1 to 18 carbon atoms, or a pharmaceutically acceptable salt thereof.

13. A compound according to claim 1, wherein X is oleoyl group and Y is amino group.

14. A compound according to claim 1, wherein X is $R_1CO-$.

* * * * *